United States Patent
Miyamoto et al.

(10) Patent No.: US 6,271,266 B1
(45) Date of Patent: *Aug. 7, 2001

(54) USE OF IDEBENONE AND ANALOGUES AGAINST β AMYLOID INDUCED CYTOTOXICITY

(75) Inventors: Masaomi Miyamoto, Hyogo; Keisuke Hirai; Giichi Goto, both of Osaka, all of (JP)

(73) Assignee: Takeda Chemical Industries, Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,463
(22) PCT Filed: Jul. 10, 1997
(86) PCT No.: PCT/JP97/02391
    § 371 Date: Nov. 9, 1998
    § 102(e) Date: Nov. 9, 1998
(87) PCT Pub. No.: WO98/02149
    PCT Pub. Date: Jan. 22, 1998

(30) Foreign Application Priority Data

Jul. 11, 1996 (JP) ................................. 8-182095

(51) Int. Cl.[7] .................................. A61K 31/185
(52) U.S. Cl. ............................................ 514/678
(58) Field of Search ............................... 314/678

(56) References Cited

U.S. PATENT DOCUMENTS 5,059,627  10/1991  Goto et al. ............... 514/688

FOREIGN PATENT DOCUMENTS 0 629 400 A1   12/1994  (EP).
   629400   *  12/1994  (JP).

OTHER PUBLICATIONS

G. Weyer et al., "Efficacy and Safety of Idebenone in the Long–Term Treatment of Alzheimer's Disease: A Double–Blind, Placebo Controlled Multicentre Study", Human Psychopharmacology, vol. 11, pp. 53–65, (1996).

N. Ranen et al., "A Controlled Trial of Idebenone in Huntington's Disease", Movement Disorders, vol. 11, No. 5, pp. 549–554, (1996).

U. Senin et al., "Idebenone in Senile Dementia of Alzheimer Type: A Multicentre Study", Arch. Geront. Geriatr, vol. 15, pp. 249–260, (1992).

T. Nabeshima, "Nerve Growth Factor Strategy and Preparation of Animal Model for Alzheimer–Type Senil Dementia", Yakugaku Zasshi, vol. 115, No. 7, pp. 499–512, (1995).

Abstract to Canonico et al., "The role of free radicals and brain aging", G. Gerontol. 42(2), pp. 71–75, 1994.*

Abstract to FR 2,703,591 A1, Oct. 14, 1994.*

* cited by examiner

Primary Examiner—Dwayne C. Jones
(74) Attorney, Agent, or Firm—Wenderoth, Lind & Ponack, L.L.P.

(57) ABSTRACT

A compound of the formula:

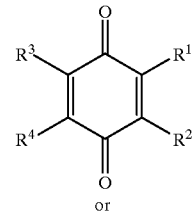

or

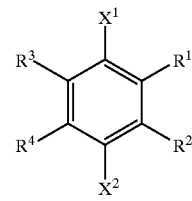

wherein $R^1$ represents a lower alkyl; $R^2$ represents H, an optionally substituted alkyl or an optionally substituted alkenyl; $R^3$ and $R^4$ each represents an optionally substituted lower alkyl or a lower alkoxy, or $R^3$ and $R^4$ form, taken together, an optionally substituted butadienylene; and $X^1$ and $X^2$ each represents an optionally esterified or etherified hydroxy, or a salt thereof is useful for protecting cells from the cytotoxicity of β-amyloid protein.

10 Claims, 3 Drawing Sheets

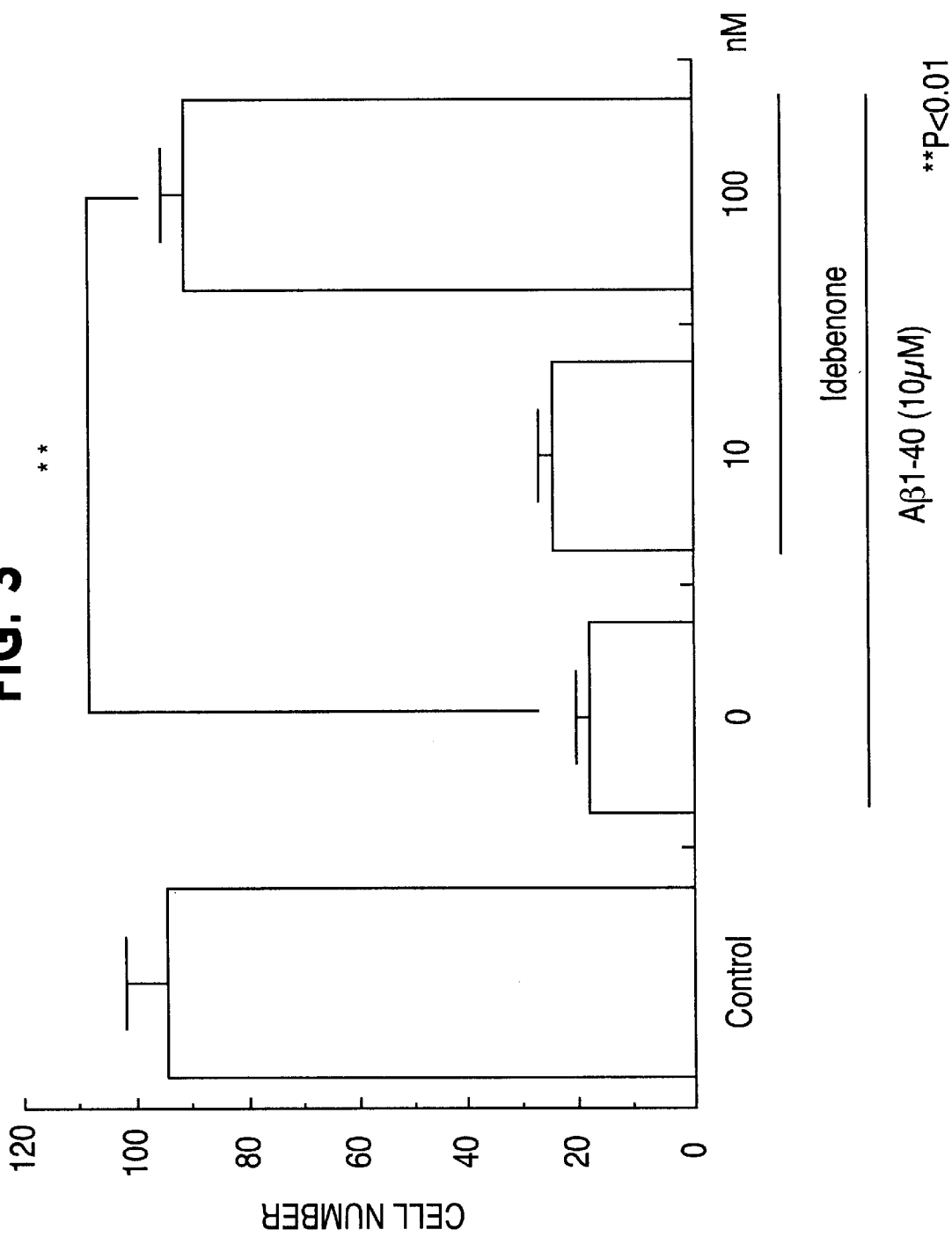

USE OF IDEBENONE AND ANALOGUES AGAINST β AMYLOID INDUCED CYTOTOXICITY

This Application is a §371 Application of PCT/JP97/02391, filed Jul. 10, 1997.

BACKGROUND OF THE INVENTION

1. FIELD OF THE INVENTION

The present invention relates to a cytoprotectant composition and more particularly to an anti-β-amyloid protein-induced cytotoxicity composition.

2. BACKGROUND ART

It is known that the cells constituting a living matter are under constant exposure to many various unfavorable factors, endogenous and exogenous, with the result that they are sometimes prevented from functioning normally or physically injured, thus undergoing degeneration and even apoptosis. Moreover, the various diseases caused by such cytological changes are serious contemporary social concerns.

The most important neuropathological feature of the brain of patients with Alzheimer's disease is senile plaques. The senile plaque contains a variety of substances but its dominant contents are β-amyloid proteins of 40 to 43 amino acid residues in length [Cell, 52, 307–308, 1988 and Neuron, 6, 487–498, 1991].

It has been demonstrated in experiments using cultured nerve cells that β-amyloid as such shows neuronal toxicity [Brain Research, 533, 315–320, 1990 and Science, 25, 279–282, 1990] and is regarded as an etiologic factor in Alzheimer's disease. Moreover, recent research has shown that aggregation of β-amyloid proteins is essential to the expression of their toxicity [Neurobiology of Aging, 1, 587–590, 1992 and Journal of Molecular Biology, 218, 149–163, 1991].

Meanwhile, it is disclosed in JP-A-3-81218 and its corresponding U.S. Pat. No. 5,059,627 that substituted 1,4-benzoquinone derivatives and the corresponding substituted 1,4-hydroquinone derivatives have potent nerve growth factor secretion-inducing activity and are, therefore, effective in the treatment of Alzheimer's disease.

According to JP-A-7-61923 and its corresponding EP-A-629400, administration of idebenone as a therapeutic agent in high doses (270 mg–360 mg day per adult) is clinically effective in Alzheimer type senile dementia.

Arch. Gerontol. Geriatr., 15, 249–260, 1992, also, reports the efficacy of idebenone by administering 90 mg daily to adult patients with Alzheimer type senile dementia.

The Journal of pharmacology and Experimental Therapeutics, 250, 1132–1140, 1989 reports that in the rat retinal neuron-neuroblastoma hybrid N18-RE-105 cells, idebenone suppresses glutamate-induced neuronal death and exerts the neuroprotection by the reactive oxygen species scavenging activity of the compound.

Figure 1:
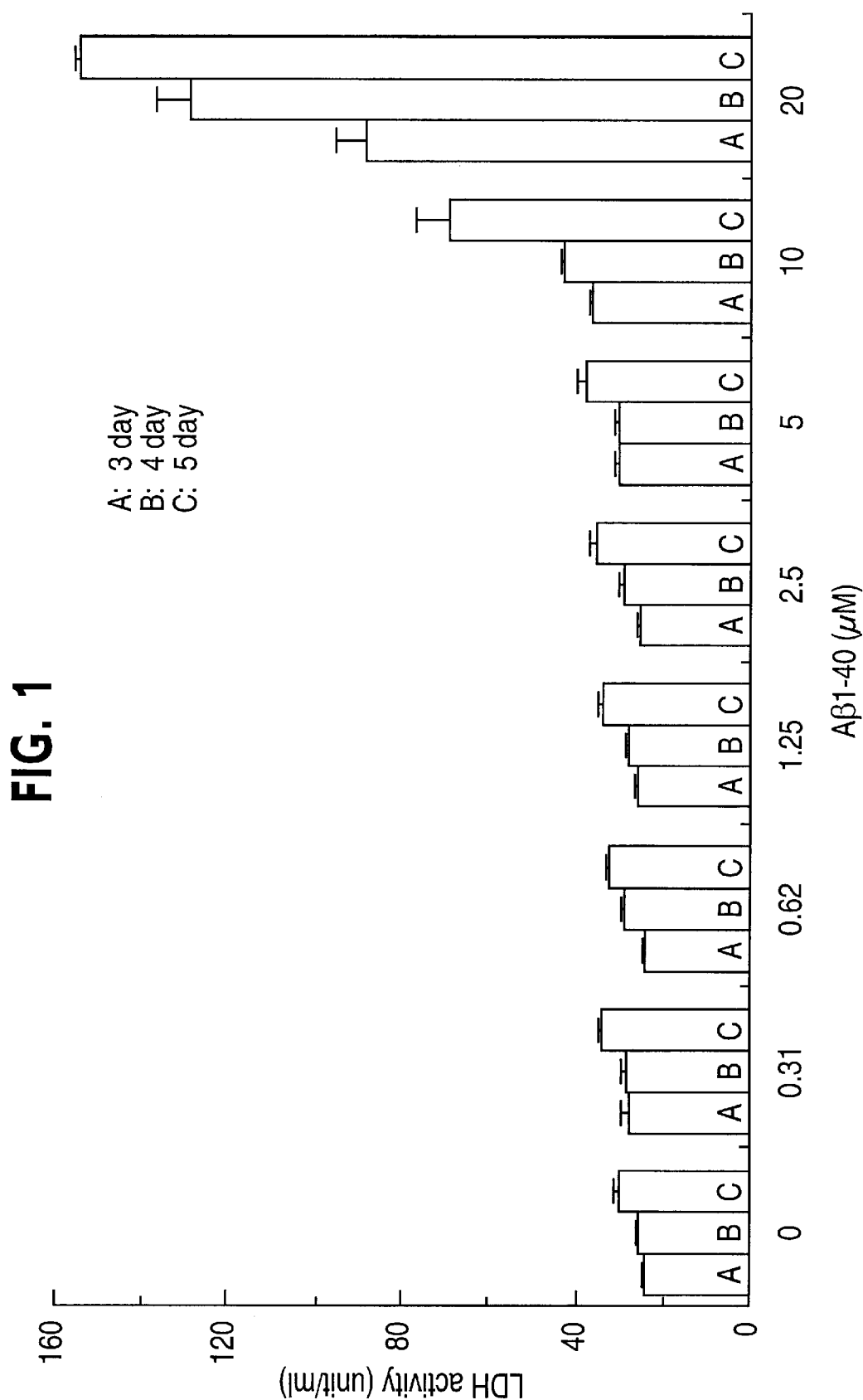
FIG. 1 is a histogram showing the correlation between the dose of Aβ1-40 and the cytotoxicological response of rat hippocampal neurons.

In the diagram, -○-represents control; -●-represents addition of idebenone (0.01 μM), -Δ-represents addition of idebenone (0.1 μM), -▲-represents addition of Aβ1-40 (10 μM), -▲-represents addition of Aβ1-40 (10 μM) and idebenone (0.01 μM), and -■-represents addition of Aβ1-40 (10 μM) and idebenone (0.1 μM).

FIG. 3 is a histogram showing the protective effect (expressed in the number of viable cells) of idebenone on Aβ1-40-induced rat hippocampal neuronal death.

SUMMARY OF THE INVENTION

It is an urgent task today to protect brain nerve cells from the cytotoxicity of β-amyloid proteins which are endogenous etiologic factors in neuronal dysfunction, injury and even apoptosis and to establish an effective prophylactic and therapeutic modality for cerebroneural diseases, particularly neurodegenerative diseases of the brain such as Alzheimer's disease and Parkinson's disease. As of today, however, no effective therapeutic and prophylactic strategy has been discovered as yet.

The inventors of the present invention endeavored to develop compounds having the property to protect cells (particularly neurons) from the cytotoxicity of β-amyloid proteins (β-amyloid protein-induced cytotoxity antagonizing action) and firstly discovered that certain substituted 1,4-benzoquinone derivatives having a specific structure and the corresponding substituted 1,4-hydroquinone derivatives have such cytoprotective activity, and are useful for medicament because of being sparingly toxic. They accordingly have perfected the present invention.

DETAILED DESCRIPTION OF THE INVENTION

The present invention is directed to:

(1) a pharmaceutical composition for protecting cells from the cytotoxicity of β-amyloid protein, which comprises a compound of the formula:

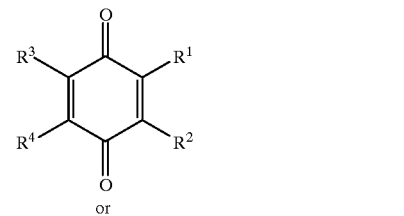

(I)

or

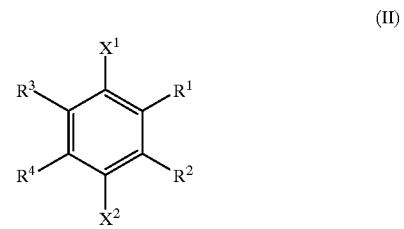

(II)

wherein $R^1$ represents a lower alkyl;
$R^2$ represents a hydrogen, an optionally substituted alkyl or an optionally substituted alkenyl;
$R^3$ and $R^4$ each represents an optionally substituted lower alkyl or a lower alkoxy, or $R^3$ and $R^4$ form, taken together, an optionally substituted butadienylene; and
$X^1$ and $X^2$ each represents an optionally esterified or etherified hydroxy [hereinafter referred to briefly as compound (I) and compound (II), respectively], or a salt thereof;

(2) a composition according to the above (1), which is for the prophylaxis or treatment of Parkinson's disease, Huntington's chorea or Creutzfeldt-Jacob disease;

(3) a composition according to the above (1), wherein
$R^1$ is a $C_{1-4}$ alkyl;
$R^2$ is (a) a hydrogen, (b) a $C_{1-22}$ alkyl which may be substituted by 1 to 10 substituents selected from the group consisting of (i) $C_{1-4}$ alkyl, (ii) hydroxy, (iii) oxo, (iv) amino, (v) mono-$C_{1-6}$ alkylamino, (vi) di-$C_{1-6}$ alkylamino, (vii) carboxy, (viii) $C_{1-4}$ alkoxy-carbonyl, (ix) $C_{6-14}$ aryl which may be substituted by 1 or 2 substituents selected from the group consisting of $C_{1-4}$ alkyl, hydroxy, carboxy and $C_{1-6}$ alkoxy-carbonyl, (x) 5- or 6-membered heterocyclic group which may be substituted by 1 or 2 substituents selected from the group consisting of $C_{1-4}$ alkyl, hydroxy, carboxy and $C_{1-6}$ alkoxy-carbonyl, and (xi) halogen, or (c) a $C_{2-15}$ alkenyl which may be substituted by 1 to 10 substituents selected from the group consisting of (i) $C_{1-4}$ alkyl, (ii) hydroxy, (iii) oxo, (iv) amino, (v) mono-$C_{1-6}$ alkylamino, (vi) di-$C_{1-6}$ alkylamino, (vii) carboxy, (viii) $C_{1-4}$ alkoxy-carbonyl, (ix) $C_{6-14}$ aryl which may be substituted by 1 or 2 substituents selected from the group consisting of $C_{1-4}$ alkyl, hydroxy, carboxy and $C_{1-6}$ alkoxy-carbonyl, (x) 5- or 6-membered heterocyclic group which may be substituted by 1 or 2 substituents selected from the group consisting of $C_{1-4}$ alkyl, hydroxy, carboxy and $C_{1-6}$ alkoxy-carbonyl, and (xi) halogen;
$R^3$ and $R^4$ each is a $C_{1-6}$ alkyl which may be substituted by 1 to 3 substituents selected from the group consisting of hydroxy, halogen, nitro, $C_{1-3}$ alkyl which may be halogenated, carboxy, $C_{1-6}$ alkoxy-carbonyl, 3-pyridyl, 1-imidazolyl and 5-thiazolyl or a $C_{1-3}$ alkoxy;
or $R^3$ and $R^4$ form, taken together with the respective adjacent carbon atoms, a benzene ring which may be substituted by 1 to 3 substituents selected from the group consisting of $C_{1-3}$ alkyl, $C_{1-3}$ alkoxy, hydroxy, nitro and halogen; and
$X^1$ and $X^2$ each is hydroxy, $C_{2-10}$ alkanoyl, benzoyl, nicotinoyl which may be quanternized, succinic acid hemi-acyl, $C_{1-8}$ alkoxy, $C_{7-13}$ aralkyloxy, tetrahydropyranyloxy or tetrahydrofuryloxy;
(4) a composition according to the above (1), wherein $R^1$ is a $C_{1-3}$ alkyl, $R^2$ is a $C_{6-14}$ alkyl substituted by hydroxy, $R^3$ and $R^4$ each is a $C_{1-3}$ alkoxy, and $X^1$ and $X^2$ each is hydroxy;
(5) a composition according to the above (1), which comprises a compound of the formula:

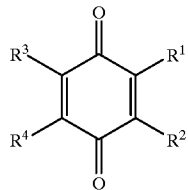

wherein all symbols are as defined above or a salt; and
(6) a composition according to the above (1), which comprises idebenone.

Referring to the above formulas (I) and (II), the "lower alkyl" for $R^1$ includes, for example, $C_{1-4}$ alkyl such as methyl, ethyl, propyl, butyl, etc.

The "alkyl" of the "optionally substituted alkyl" for $R^2$ includes $C_{1-22}$ alkyl such as methyl, ethyl, propyl, butyl, pentyl, hexyl, heptyl, octyl, nonyl, decyl, undecyl, dodecyl, tridecyl, pentadecyl, heptadecyl, eicosyl, docosyl, etc. Preferred is straight-chain $C_{6-14}$ alkyl.

The "alkenyl" of the "optionally substituted alkenyl" for $R^2$ includes, for example, straight-chain or branched $C_{2-15}$ alkenyl such as ethenyl, 1-propenyl, 3-methyl-2-butenyl, 2,6-dimethyl-2,6-octadienyl, etc. The number of double bond(s) is usually 1 to 3 and the double bonds may be conjugated.

The substituent group for the "optionally substituted alkyl" and "optionally substituted alkenyl" includes $C_{1-4}$ alkyl (e.g. methyl, ethyl, propyl, butyl, etc.), hydroxy, oxo, amino, mono-$C_{1-6}$ alkylamino (e.g. methylamino, ethylamino, etc.), di-$C_{1-6}$ alkylamino (e.g. dimethylamino, diethylamino, etc.), carboxy, alkoxycarbonyl (e.g. $C_{1-4}$ alkoxy-carbonyl such as methoxycarbonyl, ethoxycarbonyl, propionyloxycarbonyl, butoxycarbonyl, etc.), aryl (e.g. $C_{6-14}$ aryl such as phenyl, 1-naphthyl, 2-naphthyl, indanyl, etc.), heterocyclic group (e.g. 5- or 6-membered heterocyclic groups such as 2-pyridyl, 3-pyridyl, 2-thienyl, 3-thienyl, etc.), and halogen (fluorine, chlorine, bromine, iodine), among others. Preferred is hydroxy.

When the substituent group is an aryl or heterocyclic group, they may have 1 or a plurality of substituents in optional nuclear positions, which substituents include, for example, $C_{1-4}$ alkyl (e.g. methyl, ethyl, propyl, butyl, etc.), hydroxy, carboxy, and $C_{1-6}$ alkoxy-carbonyl (e.g. methoxycarbonyl, ethoxycarbonyl, propoxycarbonyl, butoxycarbonyl, etc.), among others.

The number of substituents which may be present on the "alkyl" or "alkenyl" is not limited unless detrimental to the object of the invention but may range generally from 1 to 10, preferably 1 to 6. It is also permissible that the same carbon atom is substituted by the same or different substituent groups. For example, two methyl groups and one hydroxy group may be involved.

Those substituent groups may be present in any substitutable position, and the preferred position may, for example, be 1-position or ω-position.

The "lower alkyl" of the "optionally substituted lower alkyl" for $R^3$ or $R^4$ includes, for example, $C_{1-6}$ alkyl such as methyl, ethyl, propyl, i-propyl, butyl, i-butyl, sec-butyl, t-butyl, amyl, and hexyl. Particularly preferred is $C_{1-3}$ alkyl. The substituent group for the "optionally substituted lower alkyl" includes, for example, hydroxy, halogen (e.g. fluorine, chlorine, bromine, iodine), nitro, optionally halogenated $C_{1-3}$ alkyl (e.g. trifluoromethyl etc.), carboxy, $C_{1-6}$ alkoxy-carbonyl (e.g. methoxycarbonyl, ethoxycarbonyl, etc.), 3-pyridyl, 1-imidazolyl, 5-thiazolyl, etc.

The "lower alkoxyl" for $R^3$ or $R^4$ includes, for example, $C_{1-3}$ alkoxy such as methoxy, ethoxy, propoxy, and i-propoxy.

Where $R^3$ and $R^4$ jointly represent a butadienylene, they may form a benzene ring in combination with the respective adjacent carbon atoms and the benzene ring so formed may have 1 to 3 substituents in any optional nuclear position. The substituents mentioned just above may, for example, be lower ($C_{1-3}$)alkyl (e.g. methyl, ethyl, propyl, etc.), lower ($C_{1-3}$)alkoxy (e.g. methoxy, ethoxy, propoxy, etc.), hydroxy, nitro, and halogen.

Referring to the above formula (II), the "esterified hydroxy" for $X^1$ or $X^2$ includes, for example, carboxylic acid-derived acyloxy and phosphoric acid-derived acyloxy groups. The carboxylic acid-derived acyl group of the carboxylic acid-derived acyloxy includes acyclic or cyclic $C_{2-10}$ alkanoyl groups such as formyl, acetyl, propionyl, isobutyryl, decanoyl, cyclopentyl, cyclohexylcarbonyl, etc., arylcarbonyl such as benzoyl, nicotinoyl which may be quaternized, succinic acid hemi-acyl, etc.

The "etherified hydroxy" for $X^1$ or $X^2$ includes, for example, alkoxy and aralkyloxy. The alkoxy includes $C_{1-8}$ alkoxy such as methoxy(methoxy), ethoxy, propoxy, i-propoxy, butoxy, i-butoxy, t-butoxy, sec-butoxy, amyloxy (pentyloxy), hexyloxy, tetrahydropyranyloxy, tetrahydrofuryloxy, etc. Particularly preferred is $C_{1-3}$ alkoxy. The aralkyloxy mentioned above may, for example, be $C_{7-13}$ aralkyloxy such as benzyloxy.

Among the compound (I), the compound wherein $R^1$ is a $C_{1-3}$ alkyl, $R^2$ is a $C_{6-14}$ alkyl substituted by a hydroxy, $R^3$ is a $C_{1-3}$ alkoxy and $R^4$ is a $C_{1-3}$ alkoxy, is preferred.

Among the compound (II), the compound wherein $R^1$ is a $C_{1-3}$ alkyl, $R^2$ is a $C_{6-14}$ alkyl substituted by a hydroxy, $R^3$ is a $C_{1-3}$ alkoxy, $R^4$ is a $C_{1-3}$ alkoxy, $X^1$ is a hydroxy and $X^2$ is a hydroxy, is preferred.

Among those compounds (I) and (II), the compounds with good central transfer kinetics are preferred. A specific example is idebenone.

Idebenone is a compound described in JP Koho S62-3134 (JP-B-87-3134) and its chemical name is 6-(10-hydroxydecyl)-2,3-dimethoxy-5-methyl-1,4-benzoquinone.

Depending on the kinds of substituent groups present, compounds (I) and (II) may respectively form salts, such as salts with inorganic bases, salts with organic bases, salts with inorganic acids, salts with organic acids, and salts with basic or acidic amino acids. The preferred salts with inorganic bases are, for example, salts with alkali metals such as sodium, potassium, etc., salts with alkaline earth metals such as calcium, magnesium, barium, etc., aluminum salts, and ammonium salts. The preferred salts with organic bases are salts with trimethylamine, triethylamine, pyridine, picoline, ethanolamine, diethanolamine, triethanolamine, dicyclohexylamine, N,N'-dibenzylethylenediamine, etc. The preferred salts with inorganic acids are, for example, salts with hydrochloric acid, hydrobromic acid, nitric acid, sulfuric acid, phosphoric acid, etc. The preferred salts with organic acids are, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. The preferred salts with basic amino acids are, for example, salts with arginine, lysine, ornithine, etc. The preferred salts with acidic amino acids are, for example, salts with aspartic acid, glutamic acid, etc. Among those salts, pharmacologically acceptable salts are desirable.

Compounds (I) and (II), or their salts, can each be produced by the per se known production technology, for example the processes described in Chemical and Pharmaceutical Bulletin, 30, 2797, 1982; ditto, 33, 4422, 1985, JP-A-51-128932, JP-A-63-45257, JP-A-57-109739, and JP-A-61-044840 or by processes analogous thereto.

To use the compound (I) or (II), or a salt thereof, as an anti-β-amyloid protein-induced cytotoxicity composition in accordance with the present invention, it can be formulated into pharmaceutical compositions by the per se known pharmaceutical procedures disclosed in inter alia JP Koho H1-12727(JP-B-89-12727), JP Koho S63-51123(JP-B-88-51123), JP Koho H1-39405(JP-B-89-39405), and JP-A-3-81212 or any procedures analogous thereto and administered in such dosage forms (e.g. tablets, capsules, fine granules, granules, powders, etc.), either orally or otherwise, to man and other animals.

The pharmacologically acceptable carriers which are generally used in pharmaceutical practice can be employed for the purposes of the invention. They may be organic or inorganic carriers selected from among the known excipients, binders, disintegrators, lubricants, and other pharmaceutical auxiliaries.

The excipient that can be used includes but is not limited to lactose, sucrose, D-mannitol, starch, corn starch, crystalline cellulose, light silicic acid, glucose, sorbitol, talc, and cyclodextrin. The binder includes but is not limited to crystalline cellulose, sucrose, D-mannitol, dextrin, hydroxypropylcellulose, hydroxypropylmethylcellulose, polyvinylpyrrolidone, starch, cane sugar, gelatin, methylcellulose, carboxymethylcellulose sodium, gum arabic, and polyethylene glycol. The disintegrator includes but is not limited to starch, carboxymethylcellulose, and carboxymethylcellulose calcium. The lubricant includes but is not limited to magnesium stearate, calcium stearate, talc, and colloidal silica.

The pharmaceutical composition of the present invention may be provided in controlled release dosage forms which can be manufactured by the Per se known production technology. Such controlled release dosage forms can be obtained typically by coating the tablets, granules, fine granules, or capsules with a coating composition containing a suitable amount of oil (e.g. triglyceride), polyglycerin fatty acid ester, hydroxypropylcellulose, or other coating agent.

The dosage depends on the type and manifestations of the disease to be treated but when the drug is to be administered orally for protecting nerve cells against the cytotoxicity of β-amyloid proteins, for instance, the daily dosage per human adult (b. wt. 60 kg) as compound (I) or (II) or a salt thereof is 10 mg–5000 mg, preferably 180 mg–1500 mg, and more preferably 270 mg–1440 mg. The dosage may be adjusted according on the type and severity of disease.

The anti-β-amyloid protein-induced cytotoxicity composition of the present invention is useful for the treatment (therapy) and prophylaxis of brain dysfunctions in man and other mammals and can be indicated in familial autonomic diseases, neurofibroma, neuroblastoma, pheochromocytoma, various types of dementia (senile dementia, Alzheimer's disease, etc.), Parkinson's disease, Huntington's chorea, Creutzfeldt-Jakob disease, bovine spongiform encephalopathy, and scrapie, among others. The protectant composition of the present invention is particularly efficacious in Alzheimer's disease, Creutzfeldt-Jakob disease, and Parkinson's disease in man and bovine spongiform encephalopathy and scrapie in animals. The composition of the present invention is also useful for amyloid neuropathy, amyloid induced diabetes (Langerhans cell protection), pancreatic cell protection, etc.

The pharmaceutical dosage form for the cytoprotective composition of the present invention may be any form that can be orally administered for the treatment of the above-mentioned diseases. Particularly preferred are tablets, fine granules, and capsules.

The formulating amount of compound (I) or (II), or a salt thereof, per tablet or capsule, for instance, is not less than about 30 mg, preferably about 30 mg–100 mg and, in the case of granules or fine granules, is not less than about 30 mg, preferably about 30 mg–100 mg, per dose.

For the therapy of the diseases in animals, particularly domestic animals such as cattle and sheep, the cytoprotectant composition of the present invention can be administered not only in the above-mentioned dosage forms but also as additions to animal rations.

The cytoprotectant composition of the present invention may contain, in addition to compound (I) or (II) or a salt thereof, other therapeutic drugs such as centrally-acting drugs (e.g. anxiolytics, hypnotics, therapeutic drugs for schizophrenia, antiparkinsonian drugs, etc.), drugs for adult diseases such as antihypertensives, antidiabetics, hypolipidemic drugs, etc. It may also be used in combination with various nootropic agents (cerebrocirculation ameliorating agents and brain metabolic activators), and acetylcholine esterase inhibitors. Moreover, the composition can be used in combination with nutritive aids such as vitamins, digestive aid-absorption promoters, gastrointestinal drugs, etc.

Compound (I) and (II), inclusive of salts thereof, are only sparingly toxic and show little side effects or toxicity even in long-term administration. For example, the acute toxicity $LD_{50}$ value of idebenone in mice is not less than 10,000 mg/kg for both sexes and in rats is not less than 10,000 mg/kg for males and about 10,000 mg/kg for females.

It is described in Human Psychopharmacology, 11, 53–65, 1996 that when idebenone was administered in a dose of 90 mg 3 times a day (270 mg per day) or 120 mg 3 times a day (360 mg per day) to patients with Alzheimer's disease for 6 months to study the time courses of liver-associated laboratory parameters, i.e. GPT and GOT, the changes were small with substantially no difference from the control values, indicating the very low toxicological potential of idebenone.

When the cytoprotectant composition of the present invention is provided as a controlled release dosage form, it is preferably administered so that the daily release of compound (I) or (II), or a salt thereof, will be at least 90 mg or preferably at least 150 mg. After the bioavailability of compound (I) or (II), or a salt thereof, has been improved, the above-mentioned release rate may be reduced accordingly.

The daily dosage of compound (I) or (II), or a salt thereof, in the pharmaceutical composition of the present invention can be given in a plurality of divided doses according to the therapeutic modality, that is to say in 2 through 6 divided doses daily. The preferred regimen is 3 divided doses a day. Each dose corresponds to the daily dosage divided by the number of doses. The dosing time is not so critical but postprandial administration, i.e. after each meal, is preferred.

BEST MODE FOR CARRYING OUT OF THE INVENTION

The following experimental and working examples are intended to describe the present invention in further detail.

EXAMPLES

Experimental Example 1

The cytoprotective (cytotoxicity antagonizing) effect of idebenone on the toxicological response of rat hippocampal neurons to β-amyloid protein 1-40 (hereinafter referred to briefly as Aβ1-40) was evaluated.

1. Method

The hippocampus isolated from the fetal rat brain was cultured for 6 days and Aβ1-40 was added to the culture to evaluate the efficacy of idebenone against Aβ1-40-induced neuronal apoptosis.

The cultured rat hippocampal neurons were prepared by the following procedure.

From the 18-day viviparous SD rat brain, the hippocampus was isolated on ice and treated with 0.25% trypsin and 0.1 mg/ml deoxyribonuclease I in Hank's solution at 37° C. for 10 minutes. The enzyme-treated cells were collected with a filter and suspended in Eagle's MEM containing 50 U/ml penicillin, 50 μg/ml streptomycin, 10% fetal calf serum, and 1% B27 Supplement (GIBCO). The suspension was diluted and seeded on a 48-well plate (COSTAR) precoated with poly-L-lysine, 100,000 cells/300 μl/well. Culture was carried out in the presence of 5% carbon dioxide gas at 37° C. On day 4 of culture, the medium was replaced with Eagle's MEM (MEM-N2) containing 50 U/ml penicillin, 50 μg/ml streptomycin, 10 mM HEPES-Na (pH 7.3) and N2 Supplement. On day 7 of culture, the medium was further replaced with MEM-N2 containing Aβ1-40 (Bachem) and the test drug, and the efficacy of the drug against the toxicity of Aβ1-40 was evaluated.

The lactate dehydrogenase (LDH) activity released extracellularly from the injured cells into the medium was assayed over 3–5 days after treatment and the toxicity was evaluated using the assayed activity as an indicator. In addition, on day 4 after addition of the drug, the cells were fixed with 4% paraformaldehyde, stained with anti-MAP2 antibody (Amersham) and randomly photographed under the microscope, and the number of neurons per visual field was counted.

2. Results

The study using the leakage of LDH activity into the medium during 3–5 days after addition of Aβ1-40 revealed that Aβ1-40 showed dose-dependent toxicity [FIG. 1].

Figure 2:
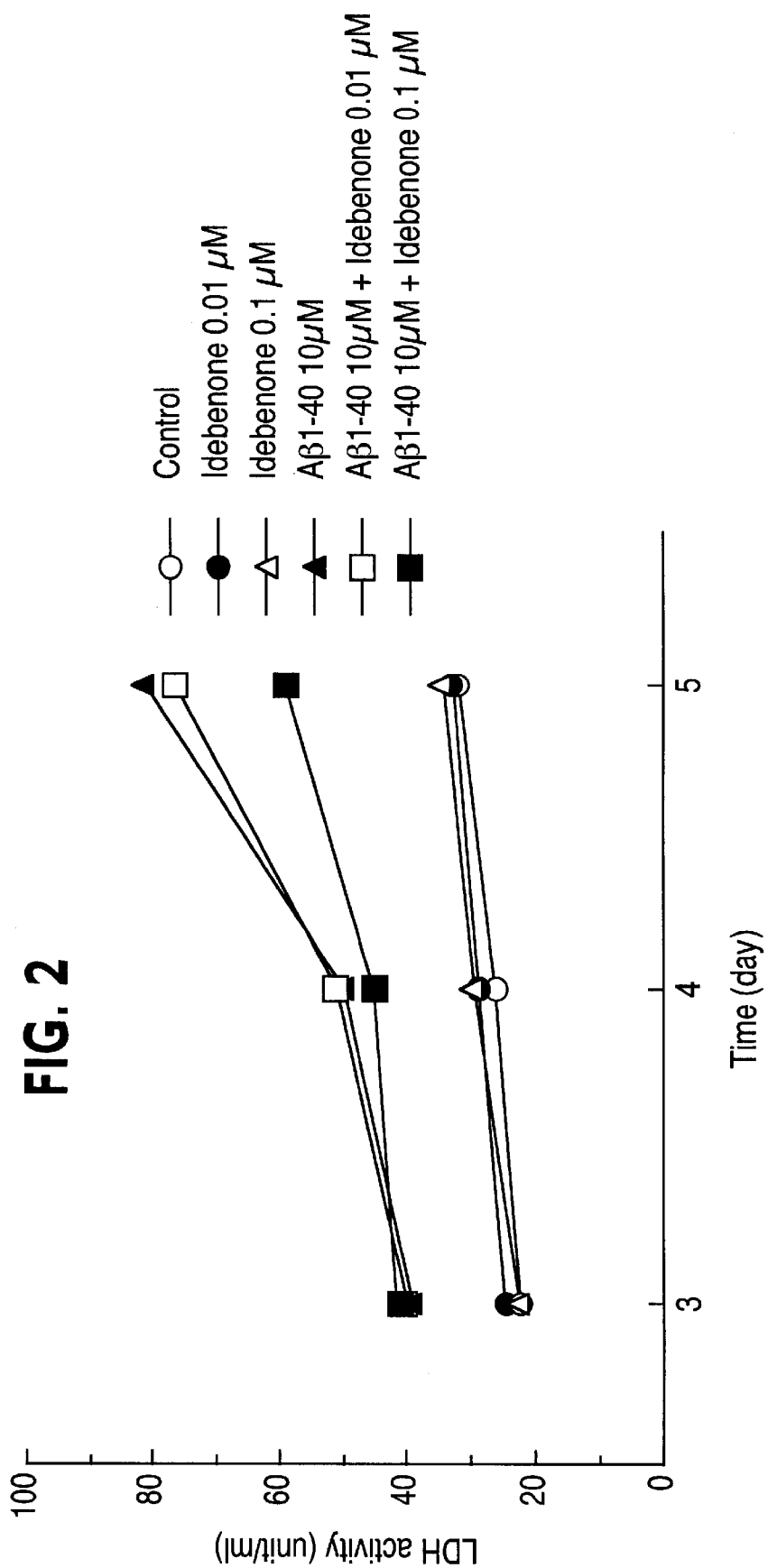
FIG. 2 is a diagrammatic representation showing the protective action of idebenone against the cytotoxic effect of Aβ1-40 (10 μM) on rat hippocampal neurons.

In contrast, idebenone 100 nM suppressed the release of LDH during 3–5 days following its addition [FIG. 2]. This result was interpreted as meaning that idebenone suppressed the toxic effect of Aβ1-40 on hippocampal neurons.

In addition, when the neurons were stained with anti-MAP2 antibody, the number of viable cells in the idebenone 100 nM group was found to be approximately equal to the number of viable cells in the control group, indicating that the drug suppressed the Aβ1-40 10 μM-caused decline in the number of neurons and inhibited neuronal death significantly (cytoprotective effect) (FIG. 3).

The above findings indicate a cytoprotective action of idebenone against the hippocampal neuronal toxicity of β-amyloid.

Example 1

Manufacture of Idebenone 90 mg Tablets

| | |
|---|---|
| Idebenone | 90.0 g |
| Lactose (EP) | 233.2 g |
| Dextrinized starch | 11.2 g |
| Carboxymethylcellulose calcium (ECG 505) | 67.3 g |
| Magnesium stearate (EP) | 1.1 g |
| Hydroxypropylmethylcellulose USP (Pharmacoat 606) | 5.6 g |
| Polyethylene glycol (NF 6000) | 1.4 g |
| Propylene glycol (EP) | 0.5 g |
| Talc (EP) | 1.8 g |
| Titanium dioxide (EP E171) | 2.7 g |
| Red color 30 (E172) | 0.2 g |
| Total | 415.0 g |

Idebenone and water were added to the above pharmaceutical excipient component and the mixture was compounded and dried. To the dry compound, the above disintegrator and lubricant components were added, and after homogenization, the mixture was compressed by means of a compression tablet machine to provide 1,000 tablets containing 90 mg of idebenone in each tablet measuring 11 mm in diameter and 4.3 mm in thickness and weighing 415 mg.

Example 2

Manufacture of Idebenone 120 mg Tablets

| | |
|---|---:|
| Idebenone | 120.0 g |
| Lactose (EP) | 203.2 g |
| Dextrinized starch | 11.2 g |
| Carboxymethylcellulose calcium (ECG 505) | 67.3 g |
| Magnesium stearate (EP) | 1.1 g |
| Hydroxypropylmethylcellulose USP (Pharmacoat 606) | 5.6 g |
| Polyethylene glycol (NF 6000) | 1.4 g |
| Propylene glycol (EP) | 0.5 g |
| Talc (EP) | 1.8 g |
| Titanium dioxide (EP E171) | 2.7 g |
| Red color 30 (E172) | 0.2 g |
| Total | 415.0 g |

Idebenone and water were added to the above pharmaceutical excipient component and the mixture was compounded and dried. To the dry compound, the above disintegrator and lubricant components were added, and after homogenization, the mixture was compressed by means of a compression tablet machine to provide 1,000 tablets containing 120 mg of idebenone in each tablet measuring 11 mm in diameter and 4.3 mm in thickness and weighing 415 mg.

INDUSTRIAL APPLICABILITY

The anti-β-amyloid protein-induced cytotoxicity composition of the present invention is a safe drug with a low toxicological potential. The disease in which the composition can be indicated with advantage includes but is not limited to familial autonomic diseases, neurofibroma, neuroblastoma, pheochromocytoma, various types of dementia, Parkinson's disease, Huntington's chorea, Creutzfeldt-Jakob disease, bovine spongiform encephalopathy, and scrapie. It is particularly efficacious in Alzheimer's disease, Creutzfeldt-Jakob disease and Parkinson's disease in man and, as far as animals are concerned, it is effective against spongiform encephalopathy in cattle and scrapie in sheep. The composition of the present invention is also useful for amyloid neuropathy, amyloid induced diabetes (Langerhans cell protection), pancreatic cell protection, etc.

What is claimed is:

1. A method of protecting cells from the cytotoxicity of β-amyloid protein in a mammal, which comprises administering to such mammal an effective amount of a compound of the formula:

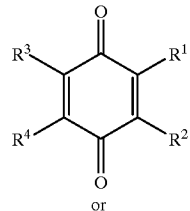

or

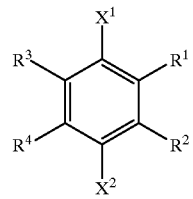

wherein $R^1$ represents a lower alkyl;

$R^2$ represents a hydrogen, an optionally substituted alkyl or an optionally substituted alkenyl;

$R^3$ and $R^4$ each represents an optionally substituted lower alkyl or a lower alkoxy, or $R^3$ and $R^4$ form, taken together, a butadienylene; and $X^1$ and $X^2$ each represents an optionally esterified or etherified hydroxy, or a salt thereof with a pharmaceutically acceptable excipient, carrier or diluent.

2. The method according to claim 1, wherein $R^1$ is a $C_{1-4}$ alkyl;

$R^2$ is (a) hydrogen, (b) a $C_{1-22}$ alkyl which may be substituted by 1 to 10 substituents selected from the group consisting of (i) $C_{1-4}$ alkyl, (ii) hydroxy, (iii) oxo, (iv) amino, (v) mono-$C_{1-6}$ alkylamino, (vi) di-$C_{1-6}$ alkylamino, (vii) carboxy, (viii) $C_{1-4}$ alkoxy-carbonyl, (ix) $C_{6-14}$ aryl which may be substituted by 1 or 2 substituents selected from the group consisting of $C_{1-4}$ alkyl, hydroxy, carboxy and $C_{1-6}$ alkoxy-carbonyl, (x) 5-or 6-membered heterocyclic group which may be substituted by 1 or 2 substituents selected from the group consisting of $C_{1-4}$ alkyl, hydroxy, carboxy and $C_{1-6}$ alkoxy-carbonyl, and (xi) halogen, or (c) a $C_{2-15}$ alkenyl which may be substituted by 1 to 10 substituents selected from the group consisting of (i) $C_{1-4}$ alkyl, (ii) hydroxy, (iii) oxo, (iv) amino, (v) mono-$C_{1-6}$ alkylamino, (vi) di-$C_{1-6}$ alkylamino, (vii) carboxy, (viii) $C_{1-4}$ alkoxy-carbonyl, (ix) $C_{6-14}$ aryl which may be substituted by 1 or 2 substituents selected from the group consisting of $C_{1-4}$ alkyl, hydroxy, carboxy and $C_{1-6}$ alkoxy-carbonyl, (x) 5- or 6-membered heterocyclic group which may be substituted by 1 or 2 substituents selected from the group consisting of $C_{1-4}$ alkyl, hydroxy, carboxy and $C_{1-6}$ alkoxy-carbonyl, and (xi) halogen;

$R^3$ and $R^4$ each is a $C_{1-6}$ alkyl which may be substituted by 1 to 3 substituents selected from the group consisting of hydroxy, halogen, nitro, $C_{1-3}$ alkyl which may be halogenated, carboxy, $C_{1-6}$ alkoxy-carbonyl, 3-pyridyl, 1-imidazolyl and 5-thiazolyl or a $C_{1-3}$ alkoxy; or $R^3$ and $R^4$ form, taken together with the respective adjacent carbon atoms, a benzene ring which may be substituted by 1 to 3 substituents selected from the group consisting of $C_{1-3}$ alkyl, $C_{1-3}$ alkoxy, hydroxy, nitro and halogen; and $X^1$ and $X^2$ each is hydroxy, $C_{2-10}$ alkanoyl, benzoyl, nicotinoyl which may be quanternized, succinic acid hemi-acyl, $C_{1-8}$ alkoxy, $C_{7-13}$ aralkyloxy, tetrahydropyranyloxy or tetrahydrofuryloxy.

3. The method according to claim 1, wherein $R^1$ is a $C_{1-3}$ alkyl, $R^2$ is a $C_{6-14}$ alkyl substituted by hydroxy, $R^3$ and $R^4$ each is a $C_{1-3}$ alkoxy, and $X^1$ and $X^2$ each is hydroxy.

4. The method according to claim 1, which comprises a compound of the formula:

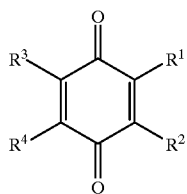

wherein all symbols are same as claim 1 or a salt.

5. The method according to claim 2, which comprises idebenone.

6. A method for the treatment of Huntington's chorea or Creutzfeldt-Jacob disease, which comprises administering to a mammal an effective amount of a compound or the formula:

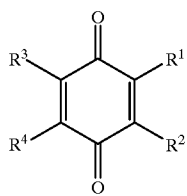

or

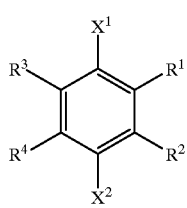

wherein $R^1$ represents a lower alkyl;

$R^2$ represents a hydrogen, an optionally substituted alkyl or an optionally substituted alkenyl;

$R^3$ and $R^4$ each represents and optionally substituted lower alkyl or a lower alkoxy, or $R^3$ and $R^4$ form, taken together, a butadienylene; and $X^1$ and $X^2$ each represents an optionally esterified or etherified hydroxy, or salt thereof with a pharmaceutically acceptable excipient, carrier or diluent by protecting cells from the cytotoxicity of β-amyloid protein in such mammal.

7. A method of claim 6, wherein $R^1$ is a $C_{1-14}$ alkyl;

$R^2$ is (a) hydrogen, (b) a $C_{1-22}$ alkyl which may be substituted by 1 to 10 substituents form the group consisting of (i) $C_{1-4}$ alkyl, (ii) hydroxy, (iii) oxo, (iv) amino, (v) mono-$C_{1-6}$ alkylamino, (vi) di-$C_{1-6}$ alkylamino, (vii) carboxy, (viii) $C_{1-4}$alkoxy-carbonyl, (ix) $C_{6-14}$ aryl which may be substituted by 1 or 2 substituents selected form the group consisting of $C_{1-4}$ alkyl, hydroxy, carboxy and $C_{1-6}$ alkoxy-carbonyl, (x) 5- or 6-membered heterocyclic group which may be substituted by 1 or 2 substituents selected from the group consisting of $C_{1-4}$ alkyl, hydroxy, carboxy and $C_{1-6}$ alkoxy-carbonyl, and (xi) halogen, or (c) a $C_{2-15}$ alkenyl which may be substituted by 1 to 10 substituents selected from the group consisting of (i) $C_{1-4}$ alkyl, (ii) hydroxy, (iii) oxo, (iv) amino, (v) mono-$C_{1-6}$ alkylamino, (vi) di-$C_{1-6}$ alkylamino, (vii) carboxy, (viii) $C_{1-4}$ alkoxy-carbonyl, (ix) $C_{6-14}$ aryl which may by substituted by 1 or 2 substituents selected from the group consisting of $C_{1-4}$ alkyl, hydroxy, carboxy and $C_{1-6}$ alkoxy-carbonyl, (x) 5- or 6-membered heterocyclic group which may be substituted by 1 or 2 substituents selected from the group consisting of $C_{1-4}$ alkyl, hydroxy, carboxy and $C_{1-6}$ alkoxy-carbonyl, and (xi) halogen;

$R^3$ and $R^4$ each is a $C_{1-6}$ alkyl which may be substituted by 1 to 3 substitutes selected from the group consisting of hydroxy, halogen, nitro, $C_{1-3}$ alkyl which may be halogenated, carboxy, $C_{1-6}$ alkoxy-carbonyl, 3-pyridyl, 1-imidazolyl and 5-thiazolyl or a $C_{1-3}$alkoxy;

or $R^3$ and $R^4$ form, taken together with the respective adjacent carbon atoms, a benzene ring which may be substituted by 1 to 3 substituents selected from the group consisting of $C_{1-3}$ alkyl, $C_{1-3}$ alkoxy, hydroxy, nitro and halogen; and $X^1$ and $X^2$ each is hydroxy, $C_{2-10}$ alkanoyl, benzoyl, nicotinoyl which may be quartemized, succinic acid hemi-acyl, $C_{1-8}$ alkoxy, $C_{7-13}$ aralkyloxy, tetrahydropyranyloxy or tetrahydrofuryloxy.

8. The method of claim 6, wherein $R^1$ is a $C_{1-3}$ alkyl, $R^2$ is a $C_{6-14}$ alkyl substituted by hydroxy, $R^3$ and $R^4$ each is a $C_{1-3}$ alkoxy, and X' and $X^2$ are each hydroxy.

9. A method of claim 6, which comprises a compound of the formula:

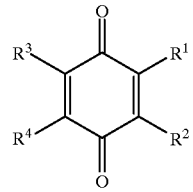

wherein all symbols are same as claim 6 or a salt.

10. The method of claim 6, which comprises idebenone.

* * * * *